US009827284B2

(12) United States Patent
Patil

(10) Patent No.: US 9,827,284 B2
(45) Date of Patent: Nov. 28, 2017

(54) METHODS FOR IMPROVING MILK LETTING DOWN IN MILCH ANIMALS

(71) Applicant: Prashant Neminath Patil, Mumbai (IN)

(72) Inventor: Prashant Neminath Patil, Mumbai (IN)

(*) Notice: Subject to any disclaimer, the term of this patent is extended or adjusted under 35 U.S.C. 154(b) by 365 days.

(21) Appl. No.: 14/498,842

(22) Filed: Sep. 26, 2014

(65) Prior Publication Data

US 2015/0017268 A1    Jan. 15, 2015

Related U.S. Application Data

(62) Division of application No. 13/501,574, filed as application No. PCT/IN2009/000572 on Oct. 12, 2009.

(51) Int. Cl.
| A23K 1/18 | (2006.01) |
| A61K 36/88 | (2006.01) |
| A61K 36/185 | (2006.01) |
| A61K 36/235 | (2006.01) |
| A61K 36/8965 | (2006.01) |
| A61K 36/39 | (2006.01) |
| A61K 36/81 | (2006.01) |
| A61K 36/24 | (2006.01) |
| A61K 36/27 | (2006.01) |
| A61K 36/31 | (2006.01) |
| A23K 10/30 | (2016.01) |
| A23K 20/10 | (2016.01) |
| A23K 20/20 | (2016.01) |
| A23K 50/10 | (2016.01) |

(52) U.S. Cl.
CPC .............. *A61K 36/81* (2013.01); *A23K 10/30* (2016.05); *A23K 20/10* (2016.05); *A23K 20/20* (2016.05); *A23K 20/30* (2016.05); *A23K 50/10* (2016.05); *A61K 36/185* (2013.01); *A61K 36/235* (2013.01); *A61K 36/24* (2013.01); *A61K 36/27* (2013.01); *A61K 36/31* (2013.01); *A61K 36/39* (2013.01); *A61K 36/88* (2013.01)

(58) Field of Classification Search
CPC .... A61K 36/185; A61K 36/235; A61K 36/27; A61K 36/31; A61K 36/39; A61K 36/81; A61K 36/88; A23K 10/30; A23K 20/10; A23K 20/20; A23K 20/30; A23K 50/10
See application file for complete search history.

(56) References Cited

U.S. PATENT DOCUMENTS

| 2,960,406 | A | * | 11/1960 | Cardon | .................. A23K 20/30 426/2 |
| 4,642,317 | A | | 2/1987 | Palmquist et al. | |
| 6,080,401 | A | | 6/2000 | Reddy et al. | |
| 6,586,018 | B1 | | 7/2003 | Fasano | |
| 8,663,623 | B2 | | 3/2014 | Patil | |
| 8,663,719 | B2 | | 3/2014 | Patil | |
| 8,668,945 | B2 | | 3/2014 | Patil | |
| 2005/0084547 | A1 | | 4/2005 | Subbiah | |
| 2012/0237622 | A1 | | 9/2012 | Patil | |
| 2012/0263697 | A1 | | 10/2012 | Patil | |
| 2012/0263811 | A1 | | 10/2012 | Patil | |
| 2012/0288578 | A1 | | 11/2012 | Patil | |

FOREIGN PATENT DOCUMENTS

| AU | WO 2007060539 A2 | * | 5/2007 | ............ A23K 40/20 |
| DE | GB 190401701 A | * | 11/1904 | |
| DE | 202006000487 | | 3/2006 | |
| DE | 202006000487 U1 | * | 3/2006 | ............ A61K 36/48 |
| DE | 102006042149 | | 5/2007 | |
| DE | 102006042149 A1 | * | 5/2007 | ............ A23K 10/30 |
| IN | WO 0203813 A1 | * | 1/2002 | ........... A23K 20/105 |
| IN | WO 2004052122 A1 | * | 6/2004 | ............ A23K 10/30 |
| IN | WO 2011045801 A1 | * | 4/2011 | ............ A23K 10/18 |
| IN | WO 2011045802 A1 | * | 4/2011 | ............ A23K 10/30 |
| IN | WO 2011055387 A2 | * | 5/2011 | ............ A23K 10/30 |
| IN | WO 2011061756 A2 | * | 5/2011 | ............ A23K 10/30 |
| JP | 11092332 A | * | 4/1999 | |
| JP | 411092332 | | 4/1999 | |
| JP | WO 0026261 A1 | * | 5/2000 | ............... C08F 6/02 |
| JP | 2007135494 A | * | 6/2007 | |
| KR | 20030044731 | | 6/2003 | |
| KR | 20030044731 A | * | 6/2003 | |
| KR | 20090097727 | | 9/2009 | |
| KR | 20090097727 A | * | 9/2009 | |
| WO | WO0074696 | | 12/2000 | |
| WO | WO 0074696 A1 | * | 12/2000 | ............ A61K 36/37 |
| WO | WO0203813 | | 1/2002 | |
| WO | WO0226261 | | 4/2002 | |
| WO | WO2004052122 | | 6/2004 | |
| WO | WO2007060539 | | 5/2007 | |
| WO | WO2011045801 | | 4/2011 | |
| WO | WO2011045802 | | 4/2011 | |
| WO | WO2011055387 | | 5/2011 | |
| WO | WO2011061756 | | 5/2011 | |

OTHER PUBLICATIONS

Kumar et al, "Use of Shatavari (*Asparagus racemosus*) as a Galactopoietic and Therapeutic herb—A Review" Agric. Rev., 2008, 29 (2), pp. 132-138.*

Sepheri, et al "Oral administration of pectin-rich plant extract enhances C3 and C4 complement concentration in woman colostrum" Reprod. Nutr. Dev. 1998, 38, pp. 255-260.*

Abhumka Herbal, "DudhNahar Granule", retrieved online: <abhumka.com/Cattle-Feed-Supplement-Granules-Biscuits-Dudhanahar.html>, Nov. 29, 2014, 3 pages.*

Chaudhury RR; Tennekoon KH, "Plants as galactagogues" Advances in international maternal and child health (Jelliffe DB, Jelliffe EF, ed.), vol. 3, Oxford Univ. Press, 1983, pp. 20-26 (abstract only).*

(Continued)

*Primary Examiner* — Chris R Tate
*Assistant Examiner* — Aaron J Kosar
(74) *Attorney, Agent, or Firm* — C. Rachal Winger

(57) ABSTRACT

The invention concerns herbal compositions which improve lactation of farmed livestock comprising an effective amount of an extract and/or at least one bioactive fraction or powder from herbs such as *Asparagus, Gossypium, Foeniculum, Lepidium, Chlorophytum, Ipomoea, Withania, Leptadenia* and optionally dicalcium phosphate, chelated minerals and/or mineral mixture.

20 Claims, No Drawings

(56) References Cited

OTHER PUBLICATIONS

Sridhar "Study to Assess the Efficacy and Safety of Galactin Vet Bolus in Lactating Dairy Cows" Mysore Journal of Agricultural Sciences, 2007, 41 (4), pp. 496-502 (13 sheets).*
Henandez, "Cottonseed", Encyclopedia of Grain Science (Wrigley et al), vol. 1, Elsevier, 2004, pp. 343-348 (ISBN 0127654917).*
Pfleiderer, Immanuel "The Cotton Family" Glimpses into the Life of Indian Plants: an Elementary Indian Botany, 1908 (reprint 2000), § I-1.1.4, pp. 10-14, ISBN 81-206-1068-7.*
Gautam Global "Herbs", Jul. 1, 2002, (retrieved online: <gautamglobal.co.in/medicine.htm>), pp. 1-3.*
Holisticonline "Vidari-kanda", retrieved online: <holisticonline.com/Herbal-Med/_Herbs/h203.htm>, 2000, 2 pages.*
Rajasthan Herbals "Safed Musli Indian Herbs", Jan. 15, 2004, retrieved online: <rajasthanherbals.com/indian-herbs/Safed-Musli.php>, 1 page.*
Castillo, et al., "Effects of Feeding Rations with Genetically Modified Whole Cottonseed to Lactating Holstein Cows", J. Dairy Sci., 2004, vol. 87, pp. 1778-1785.
iHerb.com Online, URL<http://www.iherb.com/product-reviews/himalaya-herbal-healthcare-shatavari-female-tonic-60-caplets/3742/>, 2 pages, accessed Jan. 3, 2013.
Laulhere, et al., "Iron Release and Uptake by Plant Ferritin: Effects of pH, Reduction and Chelation", BioChem, 1993, vol. 290, pp. 693-699.
Meeske, et al., "The Effect of Concentrate Supplementation on the Productivity of Grazing Jersey Cows on a Pasture Based System", South African Journal of Animal Science, 2006, 36(2), pp. 105-110.
Office Action dated Jan. 14, 2014 in U.S. Appl. No. 13/501,574.
Office Action dated Jul. 23, 2013 in U.S. Appl. No. 13/501,565.
Office Action dated Jul. 24, 2013 in U.S. Appl. No. 13/511,355.
Office Action dated Aug. 5, 2013 in U.S. Appl. No. 13/508,241.
Ravikumar, et al., "Efficacy Study of HimCal Supplementation on Milk Yield in Lactating Dairy Cows", Livestock Line, Oct. 5-8, 2008, pp. 1-9.
Restriction Requirement dated Mar. 18, 2013 in U.S. Appl. No. 13/511,355.
Restriction Requirement dated Apr. 12, 2013 in U.S. Appl. No. 13/508,241.
Restriction Requirement dated Apr. 15, 2013 in U.S. Appl. No. 13/501,565.
Restriction Requirement dated Aug. 23, 2013 in U.S. Appl. No. 13/501,574.
Search Report and Written Opinion dated May 2, 2011 in PCT Application No. PCT/IN2010/000725.
Search Report and Written Opinion dated May 2, 2011 in PCT Application No. PCT/IN2010/000726.
Search Report and Written Opinion dated Jun. 23, 2010 in PCT Application No. PCT/IN2009/000572.
Search Report and Written Opinion dated Jun. 30, 2010 in PCT Application No. PCT/IN2009/000571.
Vitacost.com Online, URL<http://www.vitacost.com/himalaya-herbal-healthcare-shatavari-female-tonic-60-caplets-1>, 3 pages, accessed Jan. 3, 2013.

* cited by examiner

METHODS FOR IMPROVING MILK LETTING DOWN IN MILCH ANIMALS

CROSS-REFERENCE TO RELATED APPLICATIONS

This application is a divisional of U.S. patent application Ser. No. 13/501,574, filed Apr. 12, 2012, which is a U.S. National Stage entry of PCT/IN2009/000572, filed Oct. 12, 2009, each of which is incorporated by reference in its entirety herein.

FIELD OF THE INVENTION

The invention relates to herbal compositions for solving problem of letting down of milk in milch animals by feeding either through the concentrate feed or feed supplement. More specifically, the present invention is related to an alternative herbal based remedy for solving problem of letting down of milk in milch animals. The herbal composition acts on central nervous system, giving stress free anxiolytic effect resulting in a smooth ejection. It makes the contraction of the cisternal cavity to facilitate milk ejection which helps the emptying of alveoli. The herbal composition increases the blood circulation in the udder which reduces the chances of occurrence of infections such as Mastitis, udder, oedema etc. The herbal composition reduces milk resurge time taken for the milk ejection after initiation of the tactile stimulus. The composition comprises an effective amount of an extract and/or at least one bioactive fraction or powder from herbs such as *Asparagus, Gossypium, Foeniculum, Lepidium, Chlorophytum, Ipomoea, Withania, Leptadenia* etc. with or without dicalcium phosphate (DCP), chelated minerals and mineral mixture; and process for the preparation of such extracts or powder and herbal compositions.

BACKGROUND OF THE INVENTION

The "Letting down" is a reflex, which is stimulated by the hormone oxytocin. The actual milking can begin after the letting down reflex has been elicited. The hormone oxytocin is required to enable milch animal to fully letting down the bulk of her milk. A sucking calf or a gentle pre-milking routine is the only way for the ilch animal to release this hormone and letting down her milk more fully.

Suckling for a short period (1-2 minutes only) before milking, to stimulate milk letting down is a common practice in many farms, but the presence of calves during milking may complicate management, specially when machine milking is used. An alternatively used in some farms is only to allow suckling after milking.

Milking stimuli, such as a sucking calf, a warm wash cloth, the regime of parlour etc., causes the release of a hormone called oxytocin. Oxytocin is released from the pituitary gland, below the brain, to begin the process of milk letting down. As a result of this hormone stimulation, the muscles begin to compress the alveoli, causing a pressure in the udder known as letting down reflex, and the milk components stored in the lumen are released into the duct system. The milk is forced down into the teat cistern from which it is milked. The letting down reflex fades as the oxytocin is degraded, within 4-7 minutes. It is very difficult to milk after this time.

Ejection of milk is accomplished by contraction of the myo-epithelial cells surrounding each alveolus. The ejection process results in a rapid transfer of milk from the lobulo-alveolar spaces into larger ducts. The flow of milk due to passive withdrawal, which is greatly increased following ejection, is commonly known as letting down. In some occasions, the intra-mammary pressure is sufficiently great to overcome the resistance of the teat sphincter so that the milk may leak from the teat. Milk ejection is a neurohormonal reflex associated with the release of oxytocin. Milk ejection reflex has a neural (afferent) and a hormonal (efferent) component.

Physical stimulation of the teats, either by the calf's suckling or the milkers hands, excite receptors from which nerve impulses are send to the posterior pituitary gland causing secretion of the hormone oxytocin. The hormone is transported via the blood to the mammary gland. Because both hormones and nerve impulses are involved in the milk ejection reflex, it is called a neurohormonal reflex. Oxytocin stimulates the contraction of the alveoli and small ducts thereby emptying the milk into the larger ducts and the cistern. Hereafter the milk can be evacuated from the udder.

The contraction of the alveoli may, to some extent, be enhanced by tactile stimuli of the udder (massaging, squeezing) the so-called tap reflex. When calves suckle, they butt at the udder in order to increase milk secretion. Manual massage of the udder during milking imitates this reflex.

The greatest amount of innervation in the mammary gland of the milch animal is in the teats. Mechanical stimulation of the teat activates pressure-sensitive nerve receptors in the skin of the teat. The nerve impulses travel to the brain through the spinothalamic nerve tract. When the cell bodies of the oxytocin-containing neurons are stimulated by these impulses originating in the teat, an action potential moves down the oxytocin-containing neurons from the cell body in the hypothalamus down the axon to the neuron ending in the posterior pituitary. This causes release of oxytocin and neurophysin into the blood. The efferent pathway starts at this point. The efferent pathway begins with the release of oxytocin into the blood. Oxytocin is released into the blood in response to action potential of nerve impulses originated in the teat. It then travels to the mammary gland and binds to protein receptor sites on the epithelial secretory cells. This results in contraction of the secretory cells and expulsion of milk from the mammary gland.

Various stressful stimuli that inhibit milk ejection are associated with increased activity of the sympathetic nervous system. Oxytocin action can be blocked by catecholamines (epinephrine and norepinephrine). The hormones are usually released in response to stressful situations and increase the tone of the smooth muscles of the mammary ducts and blood vessels. This results in the reduction of oxytocin reaching the myo-epithelial cells and partial occlusion of the mammary ducts. Moreover, epinepherin directly blocks oxytocin from binding to myo-epithelial cells. This is termed as peripheral inhibition of milk ejection. Thus, exogenous oxytocin will not cause milk ejection in animals exhibiting peripheral inhibition.

A common cause of failure to milk ejection is associated with stress. The stress inhibits the release of oxytocin from the posterior pituitary gland (central inhibition of milk ejection). Exogenous oxytocin is usually administered in these cases causing milk ejection. Based on the above discussion about peripheral and central inhibition of milk ejection, it can be stated that milk ejection occurs as a result of oxytocin release, which is normally couples with inhibition of the central and peripheral inhibitory controls. Milch animals are sensitive to changes in the environment. They may withhold the milk, if they are uncomfortable with the situation. If the animals are stressed, scared or in pain, the hormone adrenaline is secreted. This hormone causes constriction of the blood vessels, thereby hindering the supply of sufficient amount of oxytocin to the udder. Adrenaline also directly acts on the myo-epithelial cells in the alveoli by blocking the oxytocin receptors. The inhibition if milk letting down will result in the leaving of milk in the secretory parts of the udder. Continuous exposure of stress to the cattle will affect the milk production negatively. Post parturient death of calf, separation of calf after birth, change of place, owner, climatic conditions and stress due to long travel, change of milker or milking routine, application of wrong milking technique or milking machines in bad conditions are the main reasons for the milch animals to withhold the milk.

In the case of cattle which do not normally letting down milk in the absence of the calf, it is traditional practice to stimulate milk flow by very brief suckling followed by partial milking, after which the calf is allowed to suck the residual milk. Poor milk ejection can be due to impaired oxytocin release, mammary insensitivity to oxytocin or to pituitary dysfunction (Murugaiyah et al., 2001). Moreover, cow's temperament can contribute to the impaired milk ejection since stress was found to inhibit oxytocin release (Bruckmaier and Blum, 1998).

Milch animals are susceptible to shock or stress caused from nutritional deficiencies, trauma, infection or extreme environmental changes such as lot adaptation stress in animal. While such stress does not necessarily exhibit its most extreme form in shock in all cases, it nevertheless adversely affects the milch animal. Unfortunately, if animals are frightened, fear may trigger the release of the hormone adrenaline, which is an antagonist of oxytocin. Death of calves is a common reason for short lactations, as tropical milch animal often fail to letting down of milk unless stimulated by suckling. Due to this there is a decrease in the milk production.

The milk producers are not having alternative remedy for solving problem of letting down of milk in milch animals, oxytocin injection is still used for the same inspite of knowing its undesirable side effects. Moreover the biochemical half-life of injected oxytocin is very short and requires several injections. Oxytocin injection which may result into get animal habituate as well as hormonal imbalance which causes fertility problems like repeat breeding, threats of abortion and threats of uterine prolapse. Biosecurity is another problem, since many farmers use same needle for the different animals which spreads contagious diseases. A better way would be the use of a long action composition, which provided a similar response over an extended time period.

There are very few patents available for solving the problem of milk letting down in cattle and related one include U.S. Pat. No. 4,490,391, which discloses the composition for treatment of shock and stress in animals comprising equal volume amounts of solutions of sodium acetate and sodium propionate. U.S. Pat. No. 4,349,544 discloses the method for increasing the milk let down in mammals by the use of long-acting oxytocin analogs. But none of the prior art documents disclose the solving problem of letting down of milk in milch animals by using the naturally available medicinal herbs.

A significant problem with herbal medicine is that herbs are slow acting in treating an ailment. In contrast, allopathic drugs act comparatively quickly. For this reason, veterinarians prefer allopathic drugs as the effective means of treatment, even though the drugs have side effects. Clearly, it would be desirable to increase the speed by which herbal medicines act, but while maintaining the natural, herbal character of the medicine so as to avoid or minimize harmful side effects. An increasing number of people are gaining awareness of the advantages of herbal medicine together with a concern over the disadvantages of modern purified drugs. Consequently, there has been an increasing public interest in the use of herbal based compositions. Thus, many people consider herbs primarily useful as a maintenance or prophylactic treatment to be taken regularly in order to prevent onset of illness. A faster acting type of herbal medicine would create far broader utility.

Accordingly, there is a real and continuing need for an inexpensive shock and/or stress treatment composition to cattle for increasing the milk production. Hence the present inventor aims to develop the compositions and specifically to those compositions with naturally occurring herb extracts and/or bioactive fraction or powder to solve the problem of letting down of milk in milch animals without the undesired side effects. In particular, the herbal compositions, which can be fed to cattle for solving the problems letting down of milk in milch animal. The present invention provides compositions that require little technical expertise to use and may be used as a nutritional supplement for milch animal. The compositions are inexpensive and cost effective.

OBJECTS OF THE INVENTION

It is the primary object of the invention to provide herbal compositions for solving problem of letting down of milk in milch animals by feeding the composition either through the concentrate feed or feed supplement.

It is an object of the invention to develop an alternative herbal based remedy using herbal extracts and/or bioactive fraction or powder for solving problem of letting down of milk in milch animals.

It is another object of the present invention to increase milk production in milch animal by feeding the herbal composition.

It is yet another object of the present invention to increase the acceptance of milk obtained after feeding the present invention herbal compositions in comparison to milk obtained by applying an injection of oxytocin to milch animal.

It is the further object of the present herbal compositions to increase dietary intake of vitamins and minerals associated with hormone production by improving the overall nutritional status of the cattle.

It is a further object of the present invention to provide herbal compositions having a longer shelf life.

It is a further object of the present invention to develop herbal compositions, which are inexpensive and cost effective.

STATEMENT OF THE INVENTION

Herbal based feed compositions for solving problem of letting down of milk in milch animals comprising mixture of effective amount of an extract and/or bioactive fraction or powder of at least one medicinal herb. The medicinal herbs are selected from the group of *Asparagus, Gossypium, Foeniculum, Lepidium, Chlorophytum, Ipomoea, Withania* and *Leptadenia*. The above said medicinal herbs are essentially selected from the group of *Asparagus racemosus, Gossypium arboreum (herbaceum), Foeniculum vulgare, Lepidium sativum, Chlorophytum borivilianum, Ipomoea digitata, Withania somnifera* and *Leptadenia reticulata*. The above said herbal mixture comprises at least four medicinal herbs which are *Asparagus racemosus, Gossypium arboreum (herbaceum), Foeniculum vulgare* or *Chlorophytum borivilianum, Lepidium sativum* or *Ipomoea digitata*. The effective amount of an extract or bioactive fraction or powder ranges 20 to 70% (w/w) *Asparagus racemosus*, 2.5 to 25% (w/w) *Gossypium arboreum (herbaceum)*, 10 to 70% (w/w) *Foeniculum vulgare* or 10 to 70% (w/w) *Chlorophytum borivilianum*, 10 to 70% (w/w) *Lepidium sativum* or 10 to 70% (w/w) *Ipomoea digitata*. The above said effective amount of an extract or bioactive fraction or powder preferably 30 to 50% (w/w) *Asparagus racemosus*, 5 to 20% (w/w) *Gossypium arboreum (herbaceum)*, 20 to 35% (w/w) *Foeniculum vulgare* or 20 to 35% (w/w) *Chlorophytum borivilianum*, 15 to 30% (w/w) *Lepidium sativum* or 15 to 30% (w/w) *Ipomoea digitata*. The effective amount of an extract or bioactive fraction or powder more preferably 40% (w/w) *Asparagus racemosus*, 10% (w/w) *Gossypium arboreum (herbaceum)*, 25% (w/w) *Foeniculum vulgare* or 25% (w/w) *Chlorophytum borivilianum*, 25% (w/w) *Lepidium sativum* or 25% (w/w) *Ipomoea digitata*. Herbal based feed compositions for solving problem of letting down of milk in milch animals optionally comprise one or more of the ingredients selected from 5 to 50% (w/w) dicalcium phosphate, dolomite, calcite, chelated minerals and mineral mixture.

DETAILED DESCRIPTION OF THE INVENTION

The invention relates to herbal feed compositions for solving problem of letting down of milk in milch animals. More specifically, the present invention is related to an alternative herbal based composition for improving milk letting down in cattle. The herbal composition acts on central nervous system, giving stress free anxiolytic effect resulting in a smooth ejection. It makes the contraction of the cisternal cavity to facilitate milk ejection which helps the emptying of alveoli. The herbal composition increases the blood circulation in the udder which reduces the chances of occurrence of infections such as Mastitis, udder, oedema etc. The herbal composition reduces milk resurge time taken for the milk ejection after initiation of the tactile stimulus.

The invention is a synergistic formulation of an effective amount of an extract and/or at least one bioactive fraction or powder from herbs such as *Asparagus, Gossypium, Foeniculum, Lepidium, Chlorophytum, Ipomoea, Withania, Leptadenia* etc. with or without dicalcium phosphate (DCP), dolomite, calcite, chelated minerals and mineral mixture. The DCP acts as a source of calcium and phosphorous.

The compositions can be used in several forms: powdered feed form, concentrate form, blender form and base mix form.

As used herein, the term "effective amount" means an amount necessary to achieve a desired result in solving problem of letting down of milk in milch animals.

The herbal feed compositions for solving problem of letting down of milk in milch animals mainly comprises the mixture of effective amount of an extract or bioactive fraction or powder of following medicinal herbs:

1. *Asparagus racemosus*: Family—Asparagaceae
It is a tall climbing, much-branched, spiny shrub with annual woody, white-grey or brown stems armed with strong, straight or recurved spines 0.5 -1.3 cm long; rootstock short, tuberous, bearing numerous fusiform, succulent tuberous roots 30-100 cm long and 1-2 cm thick. Flowers white, fragrant, small, crowded in simple and branched racemes 5-15 cm long. Fruits globose, red when ripe, 3-lobed, 0.4-0.6 cm in diameter.

2. *Gossypium arboreum*: Family: Malvaceae
It is commonly called tree cotton, is a species of cotton native to India and Pakistan and other tropical and subtropical regions of the Old World. There is evidence of its cultivation as long ago as 2000 BC by the Harappan civilization of the Indus Valley for the production of cotton textiles. This species of cotton was introduced into East Africa by about 2000 years ago, and was grown by the Meroe civilization in Nubia, the first cotton weavers in Africa. The shrub was included in Linnaeus's Species *Plantarum* published in 1753. The holotype was also supplied by him, which is now in the Linnean Herbarium in the Swedish Museum of Natural History.

3. *Foeniculum vulgare*: Family: Apiaceae
It is also known as common fennel and generally grows upto 1.5 mts high (Encyclopedia of Common Natural Ingredients, Used in Food, Drugs, and Cosmetics, p. 169 (1980)). The dried ripe fruit of this herb is commonly called fennel seed. The plant is also known in Arabic as Shamar. The plant is found in North Africa (Egypt), India and South America.

4. *Lepidium sativum*: Family—Brassicaceae
It is a fast-growing, edible plant botanically related to watercress and mustard and sharing their peppery, tangy flavor and aroma. In some regions, garden cress is known as garden pepper cress, pepper grass or pepperwort. Garden cress is a green perennial plant used as a leaf vegetable consumed by humans typically as a garnish. Undisturbed garden cress can grow to a height of two feet with minimal maintenance. When mature, garden cress produces white flowers, and small seedpods. Garden cress is used as a medicine in India in the system of ayurveda to prevent postnatal complications. Cress may be given to pet birds such as budgerigars for a healthy and fresh treat.

5. *Chlorophytum borivilianum*: Family—Liliaceae
It is eaten as a leaf vegetable in some parts of India, and its roots are used medicinally as a sex tonic under the name safed moosli. Safed Musli was originally grown in thick forest in natural form, and is a traditional medicinal plant. Mainly its tuberous roots are used in ayurvedic medicines. Roots are used for the preparation of nutritive tonic used in general sexual weakness. Now-a-days, there is a very vast demand all over the world (Specially gulf countries and cold countries). Due to its vast demand it is very costly. Safed Musli is a herb with sub-erect leaves and tuberous root system. It can grow up to a maximum height of 1.5 ft. Tubers can grow up to a depth of 10". Safed Musli is a tiny annual herb that grows well in tropical and sub-tropical climates with altitudes up to 1500 meters. Safed Musli has its origin in the India Subcontinent.

6. *Ipomoea digitata*: Family—Convolvulaceae
The genus occurs throughout the tropical and subtropical regions of the world, and comprises annual and perennial herbaceous plants, lianas, shrubs and small trees; most of the species are twining climbing plants.

7. *Withania somnifera*: Family—Solanaceae
It is an erect, evergreen, grayish tomentose shrub 0.3-2 m tall, with fairly long, stout, fleshy, whitish-brown roots.Leaves simple, alternate or subopposite, broadly ovate, glabrous, 5-12 cm long and 2.5-7 cm wide, apex subacute, base unequal, margins entire, finely stellate-pubescent beneath; main nerves about 6 pairs; petioles 0.3-1.7 cm long. The roots are considered alternative, germicidal, aphrodisiac and diuretic; they are used in Ayurveda to treat ulcers, fever,dyspnoea, cough, consumption, dropsy, rheumatism, toxicosis and memory loss. The powdered roots mixed with equal parts of honey and ghee is thought to be beneficial for impotence or seminal debility. The roots as well as the bruised leaves are also used externally to treat ulcers, painful swellings and scabies. The total alkaloids present in the roots produce relaxant and anti spasmodic effects. The fruits and seeds are diuretic. The leaves are considered anthelmintic and bitter, and their infusion is given to relieve fever.

8. *Leptadenia reticulata*: Family—Asclepiadaceae

It is known as jivanti (or svarnajivantz) in Sanskrit literature, the name (jiv=life) indicates that the plant is considered to have the ability to bestow health and vigour. It is considered to be a rasayana and included among the 10 drugs constituting the Jivaniya gana or 'vitalising group. Found in the sub-Himalayan tracts of Punjab and Uttar Pradesh and throughout the Deccan peninsula up to an altitude of 900 m and found particularly in hedges. It is also distributed throughout Mauritius, Madagascar, Sri Lanka, the Himalayas and Burma. A twining shrub, with numerous branches, the stems of which have a cork-like, deeply cracked bark, glabrous in the younger ones. Leaves coriaceous, ovate, acute, glabrous above, finely pubescent below. Flowers greenish-yellow, in lateral or subaxillary cymes, often with small hairs. Fruit follicles may be woody. The external surface of the root is rough, white or buff coloured with longitudinal ridges and furrows, and in transverse section, the wide cork, lignified stone cell layers and medullary rays can be seen.' In commerce, the root samples vary from 3 to 10 cm in length and 1.5 to 5 cm in diameter.

TABLE 1

Details of the medicinal herbs used in herbal feed compositions for solving problem of letting down of milk in milch animals are as below:

| S.No | Latin Binomial | Common Names | Geographical Distribution | Parts Used | Quantity | Adverse Effects |
|---|---|---|---|---|---|---|
| 1 | *Asparagus racemosus* | Shatawari | Throughout India | Roots & Leaves | 20-70% Preferably 40% | None |
| 2 | *Gossypium arboreum* | Kapasbeej | Throughout India | Seeds | 2.5-25% Preferably 10% | None |
| 3 | *Foeniculum vulgare* | Badishep | North India | Seeds | 10-70% Preferably 25% | None |
| 4 | *Lepidium sativum* | Haliv | Throughout India | Seeds | 10-70% Preferably 25% | None |
| 5 | *Chlorophytum borivilianum* | Safed Musli | Maharashtra & Gujarat | Roots | 10-70% Preferably 25% | None |
| 6 | *Ipomoea digitata* | Vidarikanda | Throughout India | Roots | 10-70% Preferably 25% | None |
| 7 | *Withania somnifera* | Ashwagandha | Throughout India | Roots & Leaves | 10-70% Preferably 25% | None |
| 8 | *Leptadenia reticulata* | Jeevanti (Dori) | Throughout India | Seeds, Leaf, Root & whole plant | 10-70% Preferably 25% | None |

Process for Preparation of Herbal Feed Compositions

Method-I

The present invention herbal feed compositions are prepared by one type of method comprising the following steps:
a) Obtaining the part of medicinal herb from a group comprising leaves, bark, root and aerial parts;
b) drying the plant part of step (a);
c) powdering the dried plant material of step (b) to a coarse powder;
d) the dried and powdered plant material obtained in step (c) can be used directly to prepare the feed compositions by mixing the effective amount by weight of medicinal herb selected from the group of *Asparagus racemosus, Gossypium arboreum (herbaceum), Foeniculum vulgare, Lepidium sativum, Chlorophytum borivilianum, Ipomoea digitata, Withania somnifera* and *Leptadenia reticulata* to obtain the herbal feed composition.
e) the above herbal compositions may be added with dicalcium phosphate or dolomite or calcite or chelated minerals or mineral nutrients.

Method-II

The present invention herbal feed compositions are prepared by another type of method comprising the steps as below:
a) Obtaining the part of medicinal herb from a group comprising leaves, bark, root and aerial parts;
b) drying the plant part of step (a);
c) powdering the dried plant material of step (b) to a coarse powder;
d) extracting the powdered dried plant material at a temperature in the range of 30 to 85° C.;
e) extracting the plant material with water or alcohol or mixture of both for a period ranges from 6 hours to 6 days;
f) concentrating the obtained extract under reduced pressure at a temperature in the range of 40 to 85° C.;
g) the concentrated extract is subjected to removal of solvent;
h) mixing the effective amount by weight of above concentrated extract of medicinal herb selected from the group of *Asparagus racemosus, Gossypium* arboreum (herbaceum), Foeniculum vulgare, Lepidium sativum, Chlorophytum borivilianum, Ipomoea digitata, Withania somnifera and Leptadenia reticulata to obtain the herbal feed composition.

i) the herbal compositions may be added with dicalcium phosphate or dolomite or calcite or chelated minerals or mineral nutrients.

EXAMPLES

The following specific examples presented to illustrate the herbal feed compositions for solving problem of letting down of milk in milch animals prepared by above said method I, but do not limit the scope of the invention and additional compositions are being prepared and tested.

TABLE 2

Specific combinations prepared are as following:

A)

| Medicinal Herb | Composition (% by weight) | | | | | | | | | | | | | | | | | |
|---|---|---|---|---|---|---|---|---|---|---|---|---|---|---|---|---|---|---|
|  | I | II | III | IV | V | VI | VII | VIII | IX | X | XI | XII | XIII | XIV | XV | XVI | XVII | XVIII |
| Asparagus racemosus | 20 | 30 | 40 | 50 | 60 | 70 | 40 | 50 | 30 | 30 | 30 | 25 | 50 | 45 | 40 | 35 | 25 | 20 |
| Foeniculum vulgare | 20 | 20 | 20 | 15 | 15 | 10 | 20 | 30 | 40 | 50 | 60 | 60 | 20 | 20 | 15 | 10 | 10 | 7.5 |
| Lepidium sativum | 35 | 20 | 20 | 25 | 15 | 15 | 30 | 10 | 20 | 10 | 05 | 12.5 | 20 | 30 | 40 | 50 | 60 | 70 |
| Gossypium arboreum | 25 | 25 | 20 | 10 | 10 | 05 | 10 | 10 | 10 | 10 | 05 | 2.5 | 10 | 05 | 05 | 05 | 05 | 2.5 |

B)

| Medicinal Herb | Composition (% by weight) | | | | | | |
|---|---|---|---|---|---|---|---|
|  | I | II | III | IV | V | VI | VII |
| Asparagus racemosus | 50 | 50 | 50 | 100 | — | — | — |
| Foeniculum vulgare, | 50 | — | — | — | 100 | — | — |
| Lepidium sativum | — | 50 | — | — | — | 100 | — |
| Gossypium arboreum | — | — | 50 | — | — | — | 100 |

TABLE 3

Specific combinations prepared are as following:

A)

| Medicinal Herb | Composition (% by weight) | | | | | | | | | | | | | | | | | |
|---|---|---|---|---|---|---|---|---|---|---|---|---|---|---|---|---|---|---|
|  | I | II | III | IV | V | VI | VII | VIII | IX | X | XI | XII | XIII | XIV | XV | XVI | XVII | XVIII |
| Asparagus racemosus | 20 | 30 | 40 | 50 | 60 | 70 | 40 | 50 | 30 | 30 | 30 | 25 | 50 | 45 | 40 | 35 | 25 | 20 |
| Chlorophytum borivilianum | 20 | 20 | 20 | 15 | 15 | 10 | 20 | 30 | 40 | 50 | 60 | 60 | 20 | 20 | 15 | 10 | 10 | 7.5 |
| Ipomoea digitata | 35 | 20 | 20 | 25 | 15 | 15 | 30 | 10 | 20 | 10 | 05 | 12.5 | 20 | 30 | 40 | 50 | 60 | 70 |
| Gossypium arboreum | 25 | 25 | 20 | 10 | 10 | 05 | 10 | 10 | 10 | 10 | 05 | 2.5 | 10 | 05 | 05 | 05 | 05 | 2.5 |

B)

| Medicinal Herb | Composition (% by weight) | | | | | | |
|---|---|---|---|---|---|---|---|
|  | I | II | III | IV | V | VI | VII |
| Asparagus racemosus | 50 | 50 | 50 | 100 | — | — | — |
| Chlorophytum borivilianum | 50 | — | — | — | 100 | — | — |
| Ipomoea digitata | — | 50 | — | — | — | 100 | — |
| Gossypium arboreum | — | — | 50 | — | — | — | 100 |

TABLE 4

Specific combinations prepared are as following:

Composition (% by weight)

| Ingredient | I | II | III | IV | V | VI | VII | VIII | IX | X | XI | XII | XIII | XIV | XV | XVI | XVII | XVIII |
|---|---|---|---|---|---|---|---|---|---|---|---|---|---|---|---|---|---|---|
| *Asparagus racemosus* | 20 | 25 | 35 | 45 | 55 | 65 | 35 | 35 | 25 | 25 | 25 | 20 | 45 | 40 | 35 | 30 | 25 | 20 |
| *Foeniculum vulgare* | 15 | 25 | 20 | 15 | 15 | 10 | 30 | 25 | 20 | 30 | 50 | 50 | 10 | 20 | 15 | 10 | 10 | 7.5 |
| *Lepidium sativum* | 20 | 25 | 10 | 15 | 15 | 15 | 20 | 10 | 25 | 10 | 05 | 12.5 | 10 | 20 | 20 | 30 | 40 | 50 |
| *Gossypium arboreum* | 7.5 | 10 | 7.5 | 7.5 | 7.5 | 2.5 | 7.5 | 7.5 | 7.5 | 7.5 | 05 | 2.5 | 7.5 | 05 | 05 | 2.5 | 2.5 | 2.5 |
| Dicalcium phosphate (DCP) | 37.5 | 15 | 27.5 | 17.5 | 7.5 | 7.5 | 7.5 | 22.5 | 22.5 | 27.5 | 15 | 15 | 27.5 | 15 | 25 | 27.5 | 22.5 | 20 |

TABLE 5

Specific combinations prepared are as following:

Composition (% by weight)

| Ingredient | I | II | III | IV | V | VI | VII | VIII | IX | X | XI | XII | XIII | XIV | XV | XVI | XVII | XVIII |
|---|---|---|---|---|---|---|---|---|---|---|---|---|---|---|---|---|---|---|
| *Asparagus racemosus* | 20 | 25 | 35 | 45 | 55 | 65 | 35 | 35 | 25 | 25 | 25 | 20 | 45 | 40 | 35 | 30 | 25 | 20 |
| *Chlorophytum borivilianum* | 15 | 25 | 20 | 15 | 15 | 10 | 30 | 25 | 20 | 30 | 50 | 50 | 10 | 20 | 15 | 10 | 10 | 7.5 |
| *Ipomoea digitata* | 20 | 25 | 10 | 15 | 15 | 15 | 20 | 10 | 25 | 10 | 05 | 12.5 | 10 | 20 | 20 | 30 | 40 | 50 |
| *Gossypium arboreum* | 7.5 | 10 | 7.5 | 7.5 | 7.5 | 2.5 | 7.5 | 7.5 | 7.5 | 7.5 | 05 | 2.5 | 7.5 | 05 | 05 | 2.5 | 2.5 | 2.5 |
| Dicalcium phosphate (DCP) | 37.5 | 15 | 27.5 | 17.5 | 7.5 | 7.5 | 7.5 | 22.5 | 22.5 | 27.5 | 15 | 15 | 27.5 | 15 | 25 | 27.5 | 22.5 | 20 |

The study is conducted on a sample of 25 cattle (buffaloes/cows) which are having the problems of letting down of milk from many days by one or the other reason and are routinely treated with injectable oxytocin. The above selected cattle are injected with injectable oxytocin for 10 days and during which the milk yield is recorded from each cattle whenever the injection is given. Then after a gap of 5 days the same above cattle are fed by the herbal composition of present invention specifically composition no. V of Table-2A at a recommended dose of 15 g/day/cattle for a period of 10 days and during which also the milk yield recorded from each cattle. The feed composition has not only solved problems letting down of milk in cattle but also shown rise in milk by 250-500 ml/day after 3 days from the date of feeding. It also solved the problems of side effects associated with giving injectable oxytocin. Hence the composition serves for solving the problem of letting down of milk in milch animals without harming the cattle in every respect and also increases the acceptance of the milk by people without doubts in their mind by producing hygienic milk.

A synergistic effect is achieved when the above said herbs are included in a composition, preferably at least four herbs over those fed without the herbal composition. Thus, one embodiment of the invention provides a method of selecting herbs for compositions according to these principles. It is an important aspect of the combination herbal preparation of the present invention that it contains a mixture of herbs, or extracts of herbs. An unexpected synergistic effect is exhibited by the various ingredients of the herbal preparation of the present invention. The strategic combination of herbs of the present invention exhibits beneficial effects when optimally combined as discussed above. The advantage of the polyherbal composition also minimizes the risk of development of drug resistance.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member can be referred to and claimed individually or in any combination with other members of the group or other elements found herein. It is anticipated that one or more members of a group can be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Specific embodiments disclosed herein can be further limited in the claims using consisting of or and consisting essentially of language. When used in the claims, whether as filed or added per amendment, the transition term "consisting of" excludes any element, step, or ingredient not specified in the claims. The transition term "consisting essentially of" limits the scope of a claim to the specified materials or steps and those that do not materially affect the basic and novel characteristic(s). Embodiments of the invention so claimed are inherently or expressly described and enabled herein.

In closing, it is to be understood that the embodiments of the invention disclosed herein are illustrative of the principles of the present invention. Other modifications that can be employed are within the scope of the invention. Thus, by way of example, but not of limitation, alternative configurations of the present invention can be utilized in accordance with the teachings herein. Accordingly, the present invention is not limited to that precisely as shown and described.

The invention claimed is:

1. A method for improving milk letting down in a milch animal comprising:
    selecting a milch animal with a let-down problem, and
    feeding an effective amount of an herbal composition to the milch animal with the let-down problem, wherein the herbal composition comprises at least four powders or extracts obtained from (i) *Asparagus racemosus*, (ii)*Gossypium arboreum*, (iii) *Foeniculum vulgare* or *Chlorophytum borivilianum*, and (iv) *Lepidium sativum* or *Ipomoea digitata*,
    thereby improving milk letting down in the milch animal with the let-down problem.

2. A method of claim 1 wherein the powder or extract in (iii) is obtained from *Foeniculum vulgare*.

3. A method of claim 2 wherein the powder or extract in (iv) is obtained from *Lepidium sativum*.

4. A method of claim 2 wherein the powder or extract in (iv) is obtained from *Ipomoea digitata*.

5. A method of claim 2 wherein the herbal composition further comprises a powder or extract obtained from *Withania somnifera*.

6. A method of claim 2 wherein the herbal composition further comprises a powder or extract obtained from *Leptadenia reticulata*.

7. A method of claim 2 wherein the herbal composition further comprises a powder or extract obtained from *Withania somnifera* and a powder or extract derived from *Leptadenia reticulata*.

8. A method of claim 2, wherein the herbal composition further comprises one or more additives in an amount, by percent weight of the herbal composition, of 5 to 50% (w/w).

9. A method of claim 1 wherein the powder or extract in (iv) is obtained from *Lepidium sativum*.

10. A method of claim 1 wherein the powder or extract in (iv) is obtained from *Ipomoea digitata*.

11. A method of claim 1 wherein the herbal composition further comprises a powder or extract obtained from *Withania somnifera*.

12. A method of claim 1 wherein the herbal composition further comprises a powder or extract obtained from *Leptadenia reticulata*.

13. A method of claim 1 wherein the herbal composition further comprises a powder or extract from *Withania somnifera* and a powder or extract obtained from *Leptadenia reticulata*.

14. A method of claim 1 wherein the herbal composition further comprises one or more additives selected from dicalcium phosphate, dolomite, calcite, and minerals.

15. A method of claim 14, wherein the minerals are chelated minerals.

16. A method for improving milk letting down in a milch animal comprising:
    selecting a milch animal with a let-down problem, and
    feeding an effective amount of an herbal composition to the milch animal with the let-down problem, wherein the herbal composition comprises at least four herbs in powder form selected from: (i) 40 to 70% (w/w) *Asparagus racemosus*, (ii) 5 to 20% (w/w) *Gossypium arboretum*, (iii) 10 to 25% (w/w) *Foeniculum vulgare* or 10 to 25% (w/w) *Chlorophytum borivilianum*, and (iv) 10 to 25% (w/w) *Lepidium sativum* or 10 to 25% (w/w) *Ipomoea digitata* wherein the combined percentage does not exceed 100%,
    thereby improving milk letting down in the milch animal with the let-down problem.

17. A method of claim 16 wherein the herb in (iii) is *Foeniculum vulgare*.

18. A method of claim 16 wherein the herb in (iv) is *Lepidium sativum*.

19. A method of claim 16 wherein the herb in (iv) is *Ipomoea digitata*.

20. A method of claim 16 further comprising one or more additives selected from dicalcium phosphate, dolomite, calcite, and minerals.

* * * * *